United States Patent [19]
Anderson et al.

[11] Patent Number: 5,528,647
[45] Date of Patent: Jun. 18, 1996

[54] X-RAY FLUORESCENCE INSPECTION APPARATUS

[75] Inventors: Robin J. Anderson, Bedfordshire; Trevor A. Nunn, Oxon, both of United Kingdom

[73] Assignee: Oxford Analytical Instruments Limited, Oxon, United Kingdom

[21] Appl. No.: 277,768

[22] Filed: Jul. 20, 1994

[30] Foreign Application Priority Data

Aug. 20, 1993 [GB] United Kingdom ................ 9317371

[51] Int. Cl.$^6$ ................................................ G01N 23/223
[52] U.S. Cl. .............................. 378/44; 378/45; 378/156
[58] Field of Search .............................. 378/44, 45, 156, 378/157, 158, 160

[56] References Cited

U.S. PATENT DOCUMENTS 3,079,499  2/1963  Long .
3,920,984  11/1975  Kirkendall et al. .................. 250/277
4,189,645  2/1980  Chaney et al. ...................... 378/157
4,393,512  7/1983  Wang ................................... 378/156
4,933,960  6/1990  Fujisaki ............................... 378/157

OTHER PUBLICATIONS

EPC Search Report dated Dec. 8, 1994.

*Primary Examiner*—Don Wong

[57] ABSTRACT

X-ray Fluorescence Inspection Apparatus comprises an X-ray tube (1) for generating X-rays having a range of energies which are directed towards a sample position. A first filter assembly (3) is mounted between the X-ray tube (1) and the sample position and is movable between at least two positions to enable the energy band of X-rays reaching the sample position to be controlled in two different ways. An X-ray monitor (8) monitors X-rays from the sample position; and a second filter assembly (6) mounted between the sample position and the monitor (8) is movable between at least two positions to enable the energy band of X-rays reaching the monitor to be controlled in two different ways.

10 Claims, 3 Drawing Sheets

X-RAY FLUORESCENCE INSPECTION APPARATUS

FIELD OF THE INVENTION

The invention relates to X-ray Fluorescence Inspection Apparatus for use, for example, in determining the content of specified elements within samples.

DESCRIPTION OF THE PRIOR ART

Oxford Instruments, Analytical Systems Division has manufactured for a number of years an X-ray Fluorescence Inspection Apparatus known as the LAB-X. In this apparatus, the sample is placed onto a turntable which moves the sample to an inspection position. A source of X-rays such as Fe55 is located adjacent to the sample position and generates X-rays which cause elements within the sample to fluoresce and generate X-rays with energies which are characteristic of the elements. These X-rays are monitored using a proportional counter or the like to determine the intensity of the X-rays at each energy and so determine the concentration of the elements in the sample.

Radioisotope sources are becoming much less acceptable environmentally and are subject to stringent conditions which vary from country to country. They are also uncontrollable and decay with time. As a result, there is a need to replace the radioisotope sources with equivalent X-ray tubes which generate X-rays in response to the excitation by electrons of a suitable target and can thus be used as a source of controlled energy and intensity which may be switched on or off at will. One of the problems with making this substitution is that X-ray tubes generate a much broader energy bandwidth of X-rays in comparison with radioisotopes.

SUMMARY OF THE INVENTION

In accordance with one aspect of the present invention, X-ray Fluorescence Inspection Apparatus comprises an X-ray tube for generating X-rays having a range of energies which are directed towards a sample position; a first filter assembly mounted between the X-ray tube and the sample position and movable between at least two positions to enable the energy band of X-rays reaching the sample position to be controlled in two different ways; an X-ray monitor for monitoring X-rays from the sample position; and a second filter assembly mounted between the sample position and the monitor and movable between at least two positions to enable the energy band of X-rays reaching the monitor to be controlled in two different ways.

We have developed a new X-ray Fluorescence Inspection Apparatus which enables X-ray tubes to be used but which generates results which are as good and usually even better than have been obtained using radioisotopes. This is achieved by providing a range of filters between the X-ray tube and the sample position and between the sample position and the monitor. In this way, a variety of different combinations of filters can be used depending upon the sample being inspected.

The filter assemblies are designed to tailor the energy spectrum to the needs of a particular application. For example the first filter assembly may be designed to limit or reduce the broad range of X-ray energies generated by the X-ray tube while the second filter assembly may be designed to attenuate one or more energy bands so that the remaining energy band or bands can be clearly detected.

One important application of the invention is to measure trace quantities (<100 ppm) of Fe in a low atomic number matrix e.g. in hydrocarbon or oxide materials. This invention can be used to advantage for such a measurement by using a first filter of Al with thickness 0.1 mm and a second filter of Mn with thickness 0.012 mm. The ability to select one or both of these filters considerably enhances the sensitivity available for such a determination.

Typically, at least one of the positions of each of the first and second filter assemblies will correspond to the absence of any filter so that the X-rays pass unfiltered through that position. In the preferred example, the first filter assembly will comprise an open position and two filters while the second filter assembly will comprise an open position and five different filters.

Another problem with using an X-ray tube is the bulk of that tube in comparison with the bulk of a conventional radioisotope source. It is important to position the tube and the monitor as close as possible to the sample to reduce problems of backscatter and absorption by the intermediate atmosphere and, importantly, to improve both the excitation and detection efficiency which further allows the use of smaller lower power X-ray tubes. Thus, although the second filter assembly could comprise a disk which is rotatable to bring the different filters into position, preferably and in accordance with the second aspect of the present invention, a filter assembly for use with a tubular X-ray monitor comprises a tubular support for mounting about the monitor, the support defining at least two X-ray filter positions and being rotatable about the monitor in use to bring a selected one of the filter positions into alignment with an X-ray receiving window of the monitor.

By providing the filter assembly in the form of a tubular support mounted about the monitor, significant reduction in the space requirement is achieved leading to a very compact product. Furthermore, this compact design provides low power, low heat dissipation, high stability and high sensitivity.

In general one of the filter positions will comprise an aperture through which X-rays pass without filtering.

It will be appreciated that filter assemblies according to the second aspect of the invention could be used with conventional X-ray Fluorescence Inspection Apparatus using radioisotope sources. However, the second aspect of the invention is particularly suitable for use as the second filter assembly in apparatus according to the first aspect of the invention.

The filter assembly could be mounted in a variety of ways about the X-ray monitor including, for example, being mounted directly to the monitor. Preferably, however, the tubular support is mounted to a housing positioned about the monitor. For example, the assembly may further comprise a set of bearings, for example roller bearings, mounted about and spaced from the X-ray monitor in use, the tubular support being rotatably mounted within the bearings whereby the monitor can be slid into and out of position within the tubular support without disassembling the filter assembly. This is a particularly convenient mounting arrangement allowing replacement of the monitor without the need to disassemble the filter assembly.

Each of the first and second filter assemblies could be manually operable but preferably the apparatus comprises first and/or second control means for controlling the position of the first and/or second filter assembly respectively. Typically, the control means could comprise stepper motors which are advantageously coupled to the filter assemblies via drive belts. Alternatively, gear arrangements could be used.

The resulting apparatus is very flexible in being able to inspect samples for a wide variety of different elements. This is achieved by suitably controlling the first and second filter assemblies and by controlling the X-ray tube. However, this flexibility can lead to complexity in operation of the apparatus. Preferably, therefore, the apparatus further comprises a control system for controlling operation of the X-ray tube and the first and second control means; an input device; and a parameter store for storing data defining the control conditions appropriate to the X-ray tube, first and second control means for each type of sample, whereby in response to entering a sample type via the input device, the control system accesses the associated group of parameters and then controls the X-ray tube, first and second control means accordingly.

The control system may include a microprocessor or be defined by hardware components.

BRIEF DESCRIPTION OF THE DRAWINGS

An example of an X-ray Fluorescence Inspection Device according to the invention will now be described with reference to the accompanying drawings, in which.

EMBODIMENT

Figure 1:
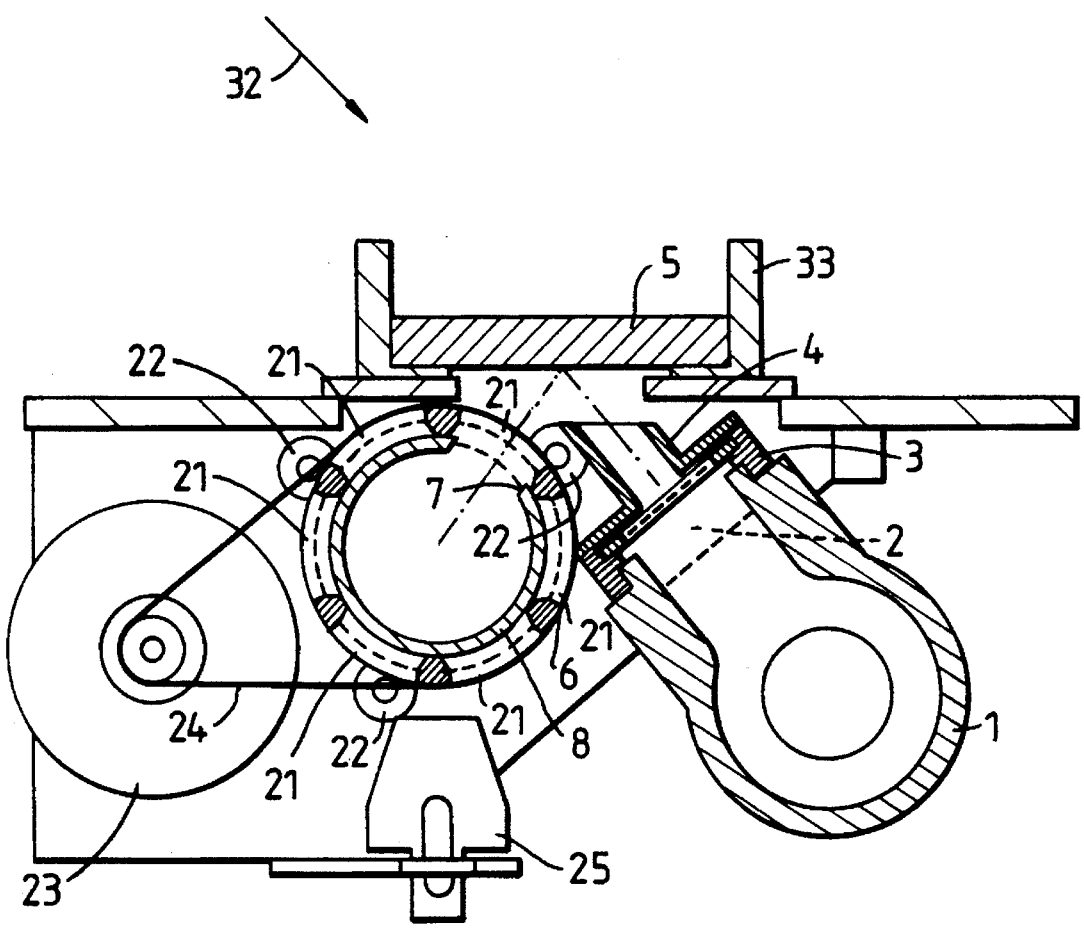
FIG. 1 is a cross-section through the analyze head of the device.

The apparatus shown in FIG. 1 is based closely on the Oxford Instruments LAB-X and only those parts of the apparatus which differ from this earlier product will be described in detail. The apparatus includes an X-ray tube 1 which includes a Rhodium target. A suitable tube is the TF1001 from the TF range of tubes manufactured by X-ray Technologies Inc. X-rays are emitted from the Be window 2 of the tube 1 and from there pass through a slide filter assembly 3 to be described in more detail below. The X-rays then pass through an aperture 4 and impinge on a sample 5 contained within a sample holder 33 of conventional form. Fluorescent X-rays emitted by the sample 5 then pass through a tubular filter assembly 6 to be described below, and then through a window 7 in a gas filled proportional counter 8. The counter 8 is connected to processing means (not shown) for computing and displaying the resultant counts in a conventional manner.

Figure 2A:
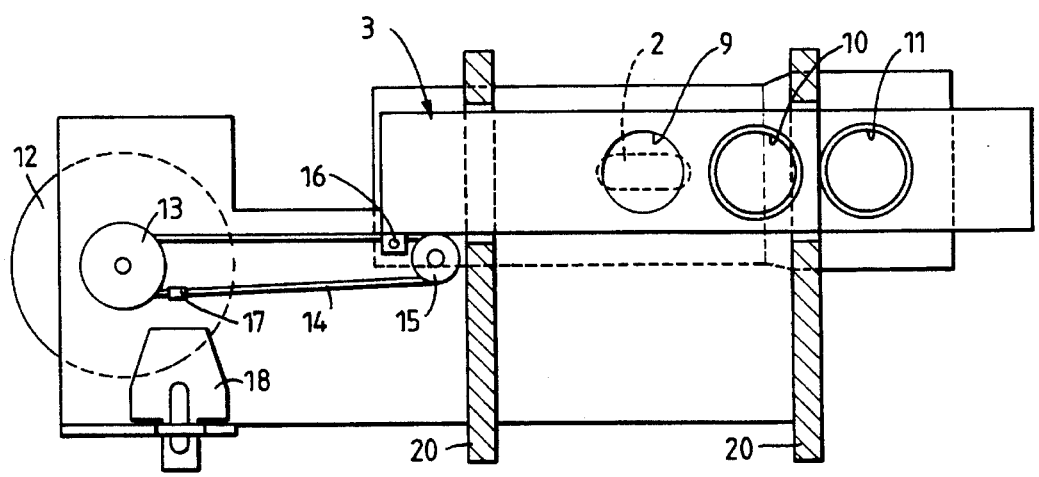
FIG. 2A is a view of the filter slide assembly shown in FIG. 1 taken in the direction X in FIG. 1 with the tube aperture removed.
Figure 2B:
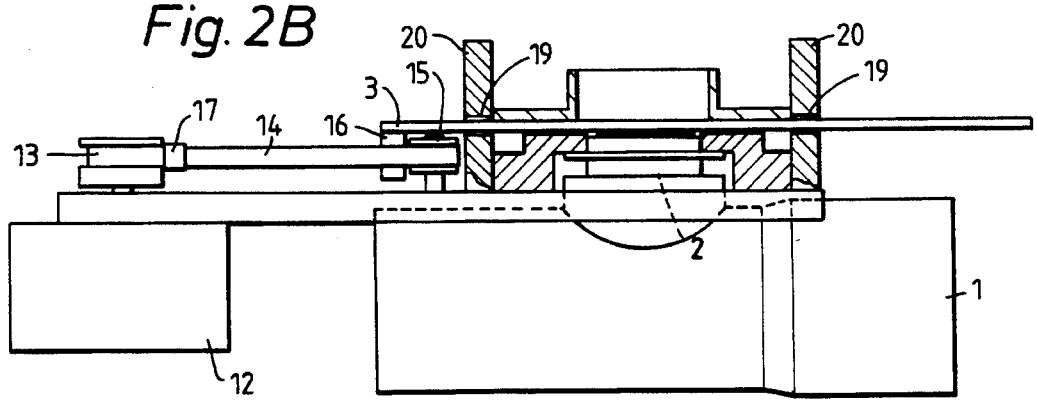
FIG. 2B is a side-view of the elements shown in FIG. 2A.

FIG. 2A illustrates in more detail the mounting of the slide filter assembly 3. As can be seen, the assembly 3 bas three circular apertures 9–11, the apertures 10,11 containing respective filters of different types. The slide assembly 3 is slidable to the left between the position shown in full lines in FIG. 2A through an intermediate position to a full leftwards position. In each of these three positions, one of the apertures 9–11 will be positioned over the window 2 of the tube 1. Movement of the slide assembly 3 is controlled by a stepper motor 12 coupled via a pulley 13 to a drive belt 14. The other end of the drive belt is entrained around an idler pulley 15. The belt 14 is attached at 16 as shown schematically in FIGS. 2A and 2B to the slide assembly 3. Rotation of the stepper motor in a clockwise direction will slide the slide assembly 3 to the right, as seen in FIGS. 2A and 2B, while rotation in an anti-clockwise direction will slide the slide assembly 3 to the left. In order to control the reference position of the slide assembly, a reflecting, e.g. metal, mark 17 is provided on the (light absorbing) belt 14 and an optical sensor 18 (shown in FIG. 2A only) is positioned at a datum location so that it can detect the presence of the mark 17 in the position shown in FIG. 2A. As can be seen in FIG. 2B, the slide assembly 3 is supported in slots 19 in respective walls 20 positioned on either side of the tube window 2.

The mounting of the slide assembly 3 allows the tube 1 to be removed without adjusting or removing the other components. Thus the critical alignment of these components is not disturbed.

The filter assembly 6 comprises a cylindrical member having six circumferentially spaced apertures 21 (FIG. 1), each having a generally rectangular form, matching the area of the proportional counter window, extending in the axial direction of the assembly. Five of the apertures 21 are provided with filters of different types and the assembly is positioned coaxially about the axis of the proportional counter 8. The assembly 6 is supported via two sets of axially spaced roller bearings, one set of which 22 is shown in FIG. 1. The roller bearings 22 are mounted to a support wall of the apparatus (not shown) so that the filter assembly 6 is spaced radially from the counter 8. This enables the assembly 6 to be rotated about the counter 8 but at the same time the counter 8 can be slid axially out from the filter assembly 6 without having to disassemble the filter assembly.

The position of the filter assembly 6 is controlled by a stepper motor 23 coupled via a belt 24 to the filter assembly 6. The assembly 6 carries a reflecting, e.g. metal, marker (not shown) which can be detected via an optical sensor 25.

In order to operate the apparatus, it is necessary to select the appropriate filter from the slide filter assembly 3, the appropriate filter from the filter assembly 6, and the voltages and currents which are to be applied to the X-ray tube 1. This will require operation of a HT source 26 (FIG. 3) and a low voltage power supply 27. Typically, the HT source 26 is adjustable from 4 kV to 25 kV in one kV steps and the low voltage source 27 is controlled to achieve an emission current in the range 10 µA to 100 µA. These sources need to be adjusted to obtain optimum count rates.

Figure 3:
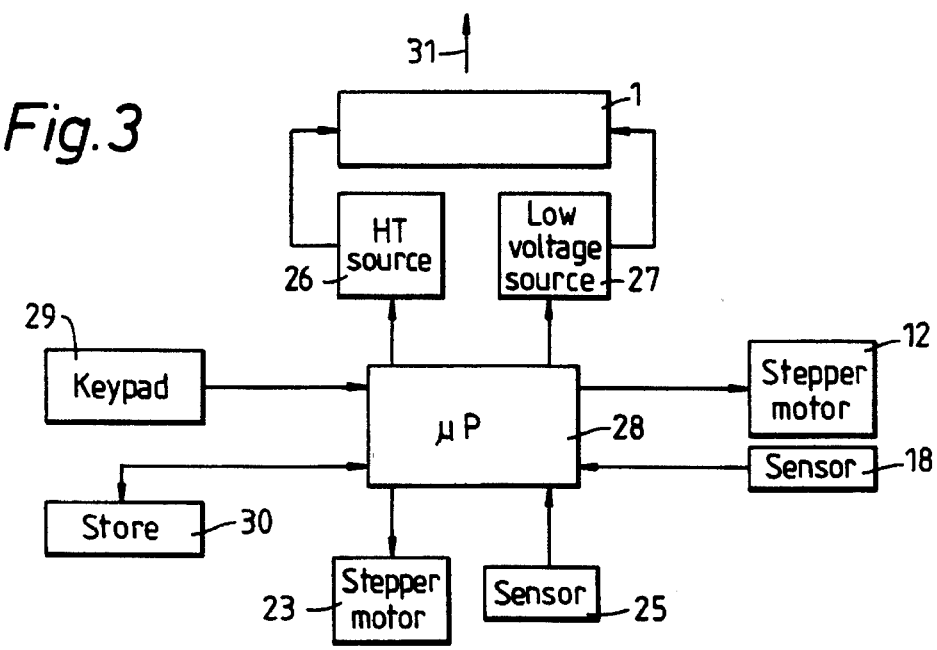
FIG. 3 is a block circuit diagram illustrating the processing components of the apparatus; and, FIG. 4 illustrates graphically the spectra obtained from an X-ray tube with and without the use of filters.

As shown in FIG. 3, control of the apparatus is achieved via a microprocessor 28 which not only controls the two sources 26,27 but also the stepper motors 12,23. The microprocessor 28 is also connected to a keypad 29, the sensors 18,25, and to a parameter store 30.

Initially, the store 30 will be loaded with sets of parameters corresponding to different applications of the apparatus. Thus, for each application, the store 30 will store values to be applied to the HT source 26 and low voltage source 27 and information concerning positions of the filter assemblies 3,6. Other parameters will also be stored, eg. calibration data, optional data processing conditions etc for analysing the resultant data.

In operation, the user will place the sample 5 in the appropriate inspection position and enter on the keypad 29 the particular application, for example the sample type. The microprocessor 28 will respond to this input by accessing the appropriate set of parameters in the store 30. The microprocessor will then actuate each stepper motor 12,23 until the corresponding optical sensor 18,25 detects the mark indicating that each filter assembly is then at its datum position. Depending upon the information from the store 30, one or both of the stepper motors 12,23 may then be activated to move the filter assemblies 3,6 to bring an alternative filter into position. Once this has been completed, the microprocessor 28 will initiate the generation of X-rays 31 by suitably controlling the sources 26,27. Thereafter, the proportional counter 8 will monitor the incoming X-rays 32 and display the results in a conventional manner.

Figure 4:
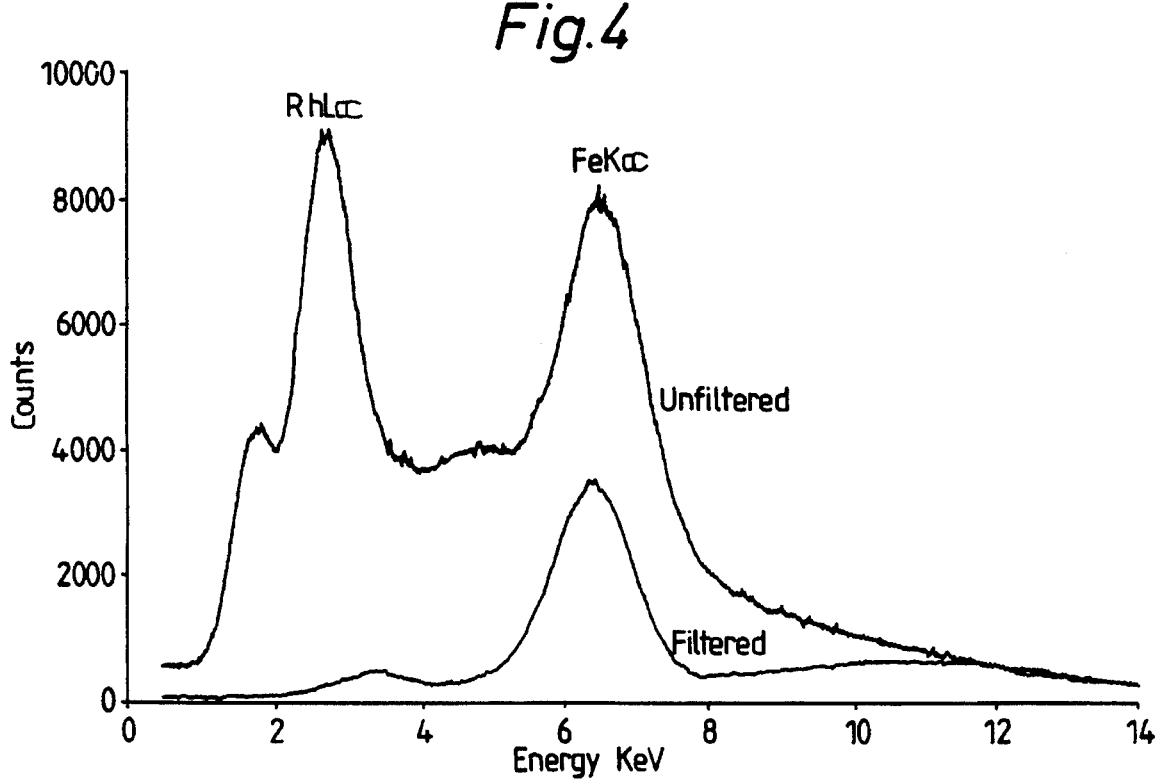

FIG. 4 illustrates the improvement in analytical performance that can be achieved by using a first filter in combination with a second filter for the determination of Fe in a silica matrix.

The pulse height distributions in FIG. 4 are from a sample containing 0.6% Fe using a Rh target tube operating at 15 kV and an Ar filled detector.

The unfiltered spectrum, taken with an emission current of 5 μA (75 mW tube power), shows the FeKα peak at 6.4 keV superimposed on a high background due to X-rays backscattered from the sample. The peak at 2.7 keV is RhLα from the X-ray tube.

The filtered spectrum was obtained using a 0.1 mm thick Al first filter and 0.012 mm thick Mn second filter and with an emission current of 15 μA. The background under the Fe peak is greatly reduced without significantly affecting the total Fe signal. The first filter reduces unwanted X-rays scattered from the tube which appear on the lower energy side of the Fe peak and the second filter absorbs X-rays on the higher energy side of the Fe peak. The total number of X-rays entering the detector is therefore reduced which enables a higher emission current to be used.

The combined effect of these filters is to lower the detection limit for Fe in a silica matrix by a factor of 3.

In the example described so far, a Rh target tube has been described. Other target tubes could also be used including Pd, Cu, Cr and Ti.

Thus, with the invention, by using suitable filters in the filter assembly 6, a signal which would otherwise be unresolvable can be resolved by absorbing the competing signal.

In some applications, a sample must be inspected in different ways to determine the presence of all elements of interest. Where this does not involve changing the X-ray tube, the change of conditions is very straightforward simply by changing the filters which are used by suitably moving the filter assemblies 3,6.

Examples of the large range of elements which can be monitored include Si on paper, S in oil, S and Ca in cement all of which can be analyzed with fixed conditions, and Al Si Ca Fe in cement which require three sequential measurements under different conditions.

In particular, the introduction of a filter over the detector window has increased the potential of Rh as a target material and has also enabled Al to be measured in the presence of high concentration of Si. This has contributed to the successful determination of $Al_2O_3$, $SiO_2$, CaO and $Fe_2O_3$ in cement.

We claim:

1. X-ray Fluorescence Inspection Apparatus comprising:

an X-ray tube for generating X-rays having a range of energies which are directed in a first direction towards a sample position so as to cause fluorescent X-rays to be generated in a second direction by a sample at the sample position, wherein the first and second directions extend on the same side of the sample position;

a first filter assembly mounted between the X-ray tube and the sample position and movable between at least two positions;

an X-ray monitor for monitoring X-rays from the sample position; and a second filter assembly mounted between the sample position and the monitor and movable between at least two positions.

2. Apparatus according to claim 1, wherein the first filter assembly comprises a slide member having at least two apertures, at least one of which includes a filter.

3. Apparatus according to claim 1, further comprising control means for controlling the position of one or both of the first and second filter assemblies.

4. Apparatus according to claim 3, wherein the or each control means comprises a stepper motor.

5. Apparatus according to claim 1, further comprising sensing means for determining the position of the first and second filter assemblies.

6. Apparatus according to claim 1, further comprising:

a control system for controlling operation of the X-ray tube and the first and second filter assemblies;

an input device; and a parameter store for storing data defining the control conditions appropriate to the X-ray tube, and the first and second filter assemblies for each type of sample, whereby in response to entering a sample type via the input device, the system accesses the associated group of parameters and then controls the X-ray tube, and the first and second filter assemblies accordingly.

7. An X-ray Fluorescence Inspection Apparatus, as set forth in claim 1, wherein the second filter assembly comprising: a tubular support mounted about the monitor, the support defining at least tow X-ray filter positions and being rotatable about the monitor to bring a selected one of the filter positions into alignment with an X-ray receiving window of the monitor.

8. An assembly according to claim 7, wherein the tubular support is mounted to a housing positioned about the monitor.

9. An assembly according to claim 8, further comprising a set of bearings mounted to the housing and spaced about the X-ray monitor in use, the tubular support being rotatably mounted within the bearings whereby the monitor can be slid into and out of position within the tubular support without disassembling the filter assembly.

10. Apparatus according to claim 1, wherein the second filter assembly comprises a tubular support for mounting about the monitor, the support defining at least two X-ray filter positions and being rotatable about the monitor to bring a selected one of the filter positions into alignment with an X-ray receiving window of the monitor.

* * * * *